(12) United States Patent
Berkow et al.

(10) Patent No.: US 7,678,057 B2
(45) Date of Patent: Mar. 16, 2010

(54) DEVICE AND SYSTEM THAT IDENTIFIES CARDIOVASCULAR INSUFFICIENCY

(75) Inventors: Jan Berkow, Morgantown, WV (US); Juan Carlos Puyana, Sewickley, PA (US); Michael Pinsky, Pittsburgh, PA (US)

(73) Assignees: Intelomed, Inc., Pittsburgh, PA (US); University of Pittsburgh - of the Commonwealth System of Higher Education, Pittsburgh, PA (US)

(*) Notice: Subject to any disclaimer, the term of this patent is extended or adjusted under 35 U.S.C. 154(b) by 755 days.

(21) Appl. No.: 11/388,661

(22) Filed: Mar. 24, 2006

(65) Prior Publication Data

US 2007/0088222 A1    Apr. 19, 2007

Related U.S. Application Data

(60) Provisional application No. 60/664,896, filed on Mar. 24, 2005.

(51) Int. Cl.
*A61B 5/02* (2006.01)

(52) U.S. Cl. .................. 600/481; 600/483; 600/485

(58) Field of Classification Search .............. 600/485, 600/509, 300, 324
See application file for complete search history.

(56) References Cited

U.S. PATENT DOCUMENTS

| | | | | |
|---|---|---|---|---|
| 5,830,131 A * | 11/1998 | Caro et al. | .................. | 600/300 |
| 6,485,431 B1 | 11/2002 | Campbell | | |
| 6,575,912 B1 * | 6/2003 | Turcott | ....................... | 600/485 |
| 6,719,705 B2 * | 4/2004 | Mills | .......................... | 600/526 |
| 6,858,006 B2 * | 2/2005 | MacCarter et al. | .......... | 600/300 |
| 7,285,090 B2 * | 10/2007 | Stivoric et al. | .............. | 600/300 |
| 7,324,848 B1 * | 1/2008 | Turcott | ........................ | 607/17 |
| 7,328,053 B1 * | 2/2008 | Diab et al. | .................. | 600/336 |
| 7,330,750 B2 * | 2/2008 | Erkkila et al. | ............... | 600/509 |
| 2005/0197675 A1 * | 9/2005 | David et al. | ..................... | 607/9 |

(Continued)

FOREIGN PATENT DOCUMENTS

WO        WO 03/077854        9/2003

(Continued)

OTHER PUBLICATIONS

Feissel, M. et al., "Respiratory Variation of Plethysmography Signal with a Pulse Oximeter . . . ", Proceedings of the American Thoracic Society, vol. 3, Apr. 2006, A295.

(Continued)

*Primary Examiner*—Robert L Nasser
*Assistant Examiner*—Michael D'Angelo
(74) *Attorney, Agent, or Firm*—Alicia M. Passerin, Esq.; Cohen & Grigsby, P.C.

(57) ABSTRACT

In an embodiment, the present invention provides a device that identifies cardiovascular dysfunction of a subject. The claimed device comprises a controller, a transducer, and a processor. The controller initiates collection of a plurality of data related to a physiological condition. The transducer collects data over a plurality of cycles and transfers the data to the processor, which reduces the received data signal into an output using a novel formula. In an example the data correlate with data that are directly related to cardiovascular dysfunction but that are of limited use.

12 Claims, 10 Drawing Sheets

U.S. PATENT DOCUMENTS

2006/0293384 A1* 12/2006 Whewell ................. 514/509
2008/0255471 A1* 10/2008 Naghavi et al. ........... 600/549

FOREIGN PATENT DOCUMENTS

WO    WO 2005/107584      11/2005

OTHER PUBLICATIONS

Ridel, C. et al., "Prediction of Fluid Responsiveness in Spontaneously Breakthing Patients . . . ", Proceedings of the American Thoracic Society, vol. 3, Apr. 2006, A295.

Lamia, B. et al., "Brachial Pulse Pressure is Related to Total Arterial Compliance and Stroke Volume in ICU Patients . . . ", Proceed. of Amer. Thor. Soc., vol. 3, Apr. 2006, A296.

Monnet, X. et al., "Measuring Aortic Diameter is Essential for Assessing Fluid . . . ", Proceedings of American Thoracic. Society., vol. 3, Apr. 2006, A296.

Zamanian, M. et al., "Assessment of Cardiac Function and Ventilatory Efficiency by Noninvasive CO2 Monitoring . . . ", Proceed. of Amer. Thor. Soc., vol. 3, Apr. 2006, A297.

Kim, H.K. et al, "Can Cadiac Contractility be Estimated by an iNspiratory Hold Maneuver?", Proceedings of American Thoracic Socity, vol. 3, Apr. 2006, A296.

Kim, H.K. et al., "Determinates of Arterial Pulse Pressure and Stroke Volume Variation during Positive-Pressure Ventilation", Proceed. of Amer. Thor. Soc., vol. 3, Apr. 2006, A297.

* cited by examiner

DEVICE AND SYSTEM THAT IDENTIFIES CARDIOVASCULAR INSUFFICIENCY

CLAIM OF PRIORITY

This invention claims the benefit of United States Provisional Application No. 60/664,896, filed on Mar. 24, 2005.

FIELD OF THE INVENTION

The invention relates to a device and system that identify systemic dysfunction in a subject, and in particular to a device and system that identify cardiovascular insufficiency.

BACKGROUND OF THE INVENTION

Despite the development of regional trauma centers, improved emergency transport systems to reduce the total time in shock, and aggressive resuscitation, trauma patient mortality and morbidity remains high. Traumatic injury is the leading cause of death in subjects <44 years of age, resulting in over 150,000 deaths annually. Severe hypovolemia due to hemorrhage is a major factor in nearly half of those deaths. Furthermore, patients who survived the initial injury are at a high risk of developing subsequent multiple organ dysfunction syndrome and sepsis with a significant rate of late mortality in the ICU. More effective patient monitoring technology would identify patients at risk to develop organ failure and guide appropriate therapy.

Current monitoring required to assess hemodynamic functionality is often invasive and is limited to high acuity settings. Non-invasive monitoring conducive to lower acuity settings, (i.e., areas of care where invasive and cumbersome monitoring techniques cannot be practically implemented) currently provides static unidimensional isolated information of questionable utility. Recent advances in our understanding of the dynamic nature of circulatory control have introduced novel hemodynamic monitoring approaches that are continuous, noninvasive and metabolic in their orientation. When these monitoring strategies are used as physiology-based feedback to guide caregiver-directed protocolized therapy, they can lead to a new and robust approach to the resuscitation of trauma patients.

This technology can potentially be exported beyond the acute care centers to many areas where less robust conditions for monitoring prevail and smaller form factors become available. This includes ambulance and life flight air transport in the civilian sector and aeromedical evacuation and critical care air transport in the military sector. The ability to provide continuous, autonomous, and quantitative hemodynamic monitoring is also conducive to telemedicine applications and appropriate for highly scalable mass causality care response.

Severe shock associated with trauma is characterized by a decreased effectiveness of circulatory blood flow to meet the metabolic demands of the body. Shock is the result of a vast array of processes with different time courses, degrees of cardiovascular compensation, monitoring needs, pathophysiologies, treatments, and outcomes. However, in all cases, prolonged and unrecognized impaired tissue perfusion will cause organ injury, increased morbidity, and death. Circulatory shock may occur from a variety of reasons, but has as its hallmark, inadequate tissue perfusion, such that ischemic dysfunction and organ injury inevitably develop. If tissue hypoperfusion is not reversed by intravascular fluid resuscitation and/or pharmacologic support aimed at restoring normal cardiac performance and vasomotor tone, organ failure and death occur. However, only half of the patients with cardiovascular insufficiency increase their cardiac output in response to volume loading. Thus, it is important to identify which patients are preload-responsive (i.e. they will increase their cardiac output in response to fluid resuscitation) because giving fluid resuscitation to a patient who is not preload-responsive will not improve their circulatory status and delay effective treatment, when delaying treatment results in organ injury and intravascular volume overload can occur in such patients which induce acute right ventricular failure (acute cor pulmonale) and pulmonary edema, both of which can compromise normal homeostatic mechanisms and induce worsening circulatory shock and death.

Thus, the prior art has at least three major deficiencies. First, the devices available to monitor a patient's systemic stability are quite insensitive. Second, the mechanisms for monitoring such patients requires that patients are either mechanically ventilated or are in an environment in which crude maneuvers may be implemented to perturb the cardiovascular system, such as by raising or abdominal compressions. Finally, the output generated by currently available devices requires competent care providers to interpret the output and to decide appropriate actions or treatment protocols. Thus, there is a need for a device that can use the insensitive signals and transform them into something meaningfully related to the subject's systemic state. There is also a need for a method that can be implemented in a spontaneously breathing subject and/or avoids the inconvenience of physical maneuvers to perturb the cardiovascular system. Finally, there is a need for a device that can be used by a lesser competent care provider, such as emergency response personnel, so that critically ill patients can receive effective treatment quickly.

SUMMARY OF THE INVENTION

The present invention meets these needs by providing a less sensitive device to assess and treat cardiovascularly unstable patients that extends the prior art by using an algorithm or formula to generate a meaningful output in order to assess and treat less sensitive devices and especially non-invasive measures are inherently less accurate and potentially less sensitive to physiologic changes. They will also be more susceptible to ambient physiological "noise" due to their superficial location (i.e., skin, mucus membrane, etc.) and the potential for dislodgement. The device may be used in a setting where there may be high acuity patients but where circumstances do not allow for complex or cumbersome and for invasive monitoring interventions such as in emergency, trauma and emergency response pre-hospital scenarios and is also useful for chronic patients, telehomecare, and as a prognostic for individuals such astronauts, firefighters, or warfighters. The invention also provides a method of using the device in spontaneously breathing subjects and/or using alternative perturbations of the cardiovascular system to enable use of a perturbation that presents an intravascular challenge. Finally, the claimed invention provides an output that maybe an interpretation of data that may also suggest appropriate treatment protocols. This is particularly important for emergency response personnel treating cardiovascularly unstable critical care patients because it enables less competent healthcare providers to quickly access and treat the patient to keep the patient alive.

In an embodiment, the claimed invention provides a novel device that identifies cardiovascular dysfunction of a subject. The claimed device comprises a controller, a transducer, and a processor. The controller initiates collection of a plurality of data related to a physiological condition such as a physiological condition of the subject's cardiovascular system. In an example, the data can be collected non-invasively. The controller may be for example, a manual or an automated switch, a plurality of software rules, or a combination thereof. The transducer collects data from the subject over a plurality of cycles and transfers the data to the processor, which reduces the received data signal into at least one output using a novel formula. In an example the collected data correlate with data that are directly related to and indicative of cardiovascular dysfunction but that are of limited use because they can only be collected via invasive techniques.

In another embodiment, the claimed invention is a method of using the claimed device.

In yet another embodiment, the claimed invention is a system.

OBJECTS OF THE INVENTION

It is an object of the present invention to provide a device and system that indicate a subject's hemodynamic dysfunction.

It is another object of the present invention to provide a device and system that indicates a cardiovascular insufficiency in a subject.

It is another object of the present invention to provide a device that is non-invasive.

It is still another object of the present invention to provide a device or a system that may be used to monitor an unattended subject.

It is yet another object of the present invention to transmit output about an unattended subject to a location that is remote to the subject.

It is still another object of the present invention to provide a device or a system that may be used to identify subjects who are dehydrated or hypovolemic.

It is yet a further object of the present invention to provide a device that collects data before and after a perturbation to the subject's cardiovascular system in order to identify a subject's cardiovascular insufficiency.

Other features, advantages, and objects of the presently disclosed invention will become apparent to those skilled in the art as a description of a presently preferred embodiment thereof proceeds.

BRIEF DESCRIPTION OF THE DRAWINGS

FIG. 2 shows schematics of examples of embodiments of the device of the claimed invention. In the example shown in FIG. 2A, the claimed device is shown in conjunction with a hospital bed. In the example shown in FIG. 2B, the claimed device is shown wrapped around a subject's leg.

DETAILED DESCRIPTION OF EMBODIMENTS OF THE INVENTION

Figure 1A:
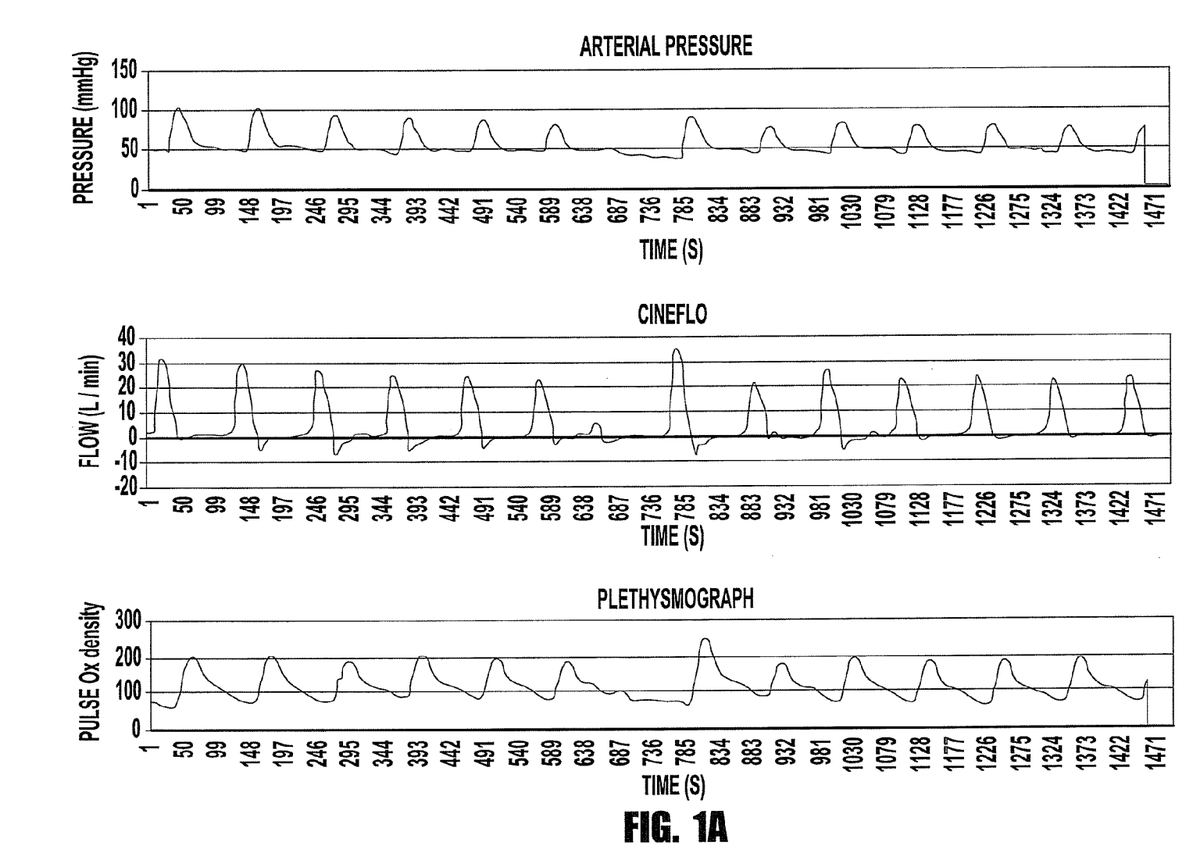
FIG. 1A shows strip chart recordings of arterial pressure, aortic flow, and pulse oximeter density during positive pressure ventilation.

The pulse density signal generated by a photoplethysmograph such as a pulse oximeter correlates with the pulsatile changes in arterial blood pressure in the same subject. This relationship is illustrated in FIG. 1A. The top chart recording is an arterial pressure trace, the middle chart recording shows aortic flow, and the bottom chart recording shows pulse density from a pulse oximeter. These data were collected from a subject undergoing coronary bypass surgery. The arterial pressure data were obtained using a femoral artery catheter and aortic flow data were obtained using a Cineflo® electromagnetic flow meter, with the flow probe positioned in the aorta. These graphs are shown to depict the strong correlation between the beat-to-beat variations in flow and arterial pressure compared to the variation in pulse density recorded from a photoplethysmograph.

Figure 1B:
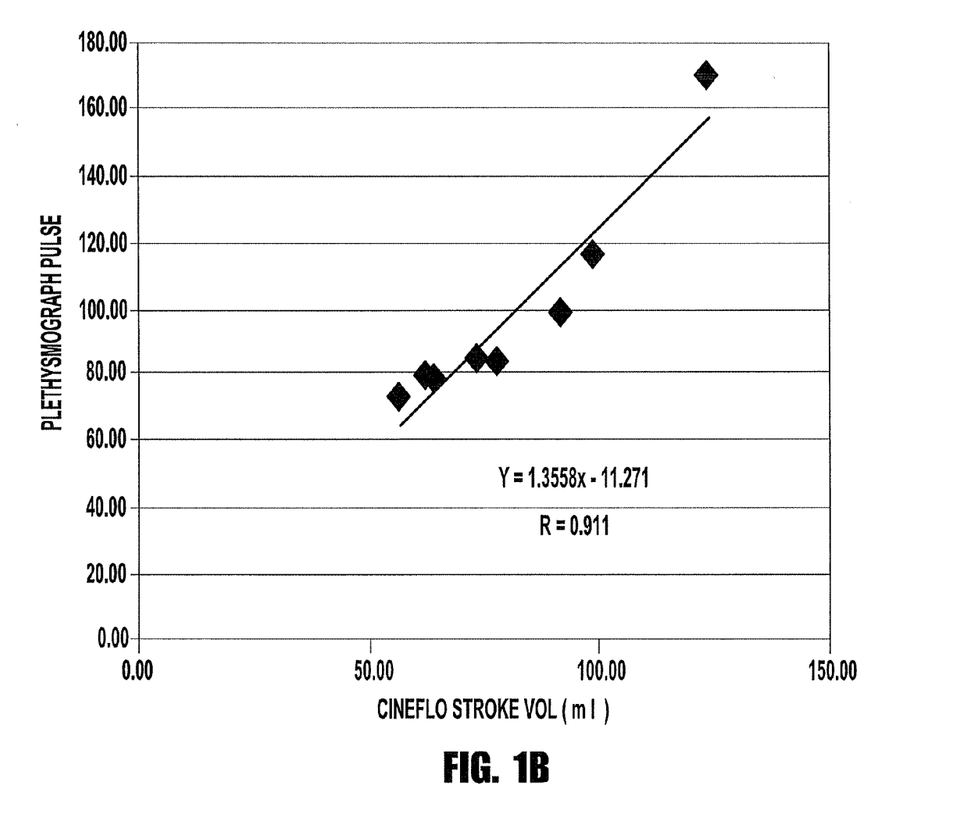
FIG. 1B shows that the pulse pressure variation signal obtained from a photoplethysmograph is significantly correlated with a measure of stroke volume variation obtained from an aortic probe.

FIG. 1B shows a graph that illustrates the significant correlation between the pulse pressure variation signal obtained from a photoplethysmograph and stroke volume as measured by a Cineflo® flow probe.

Figure 2A:
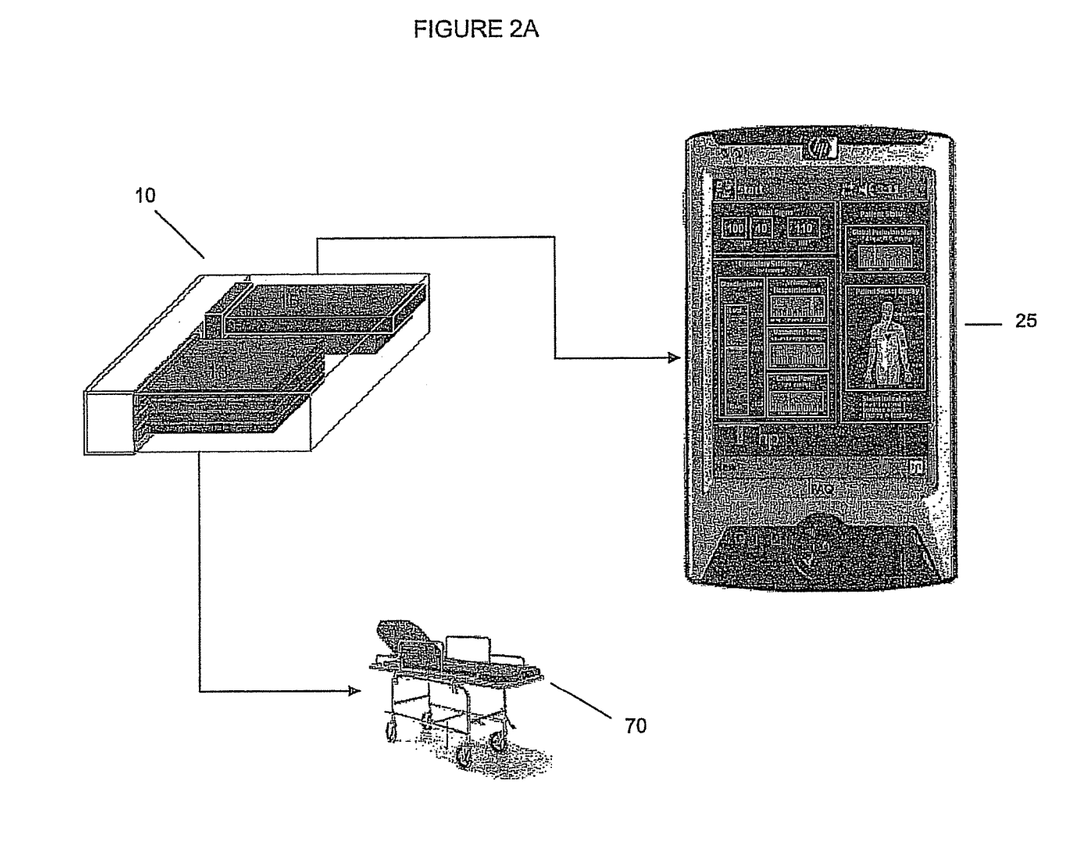
Figure 2B:
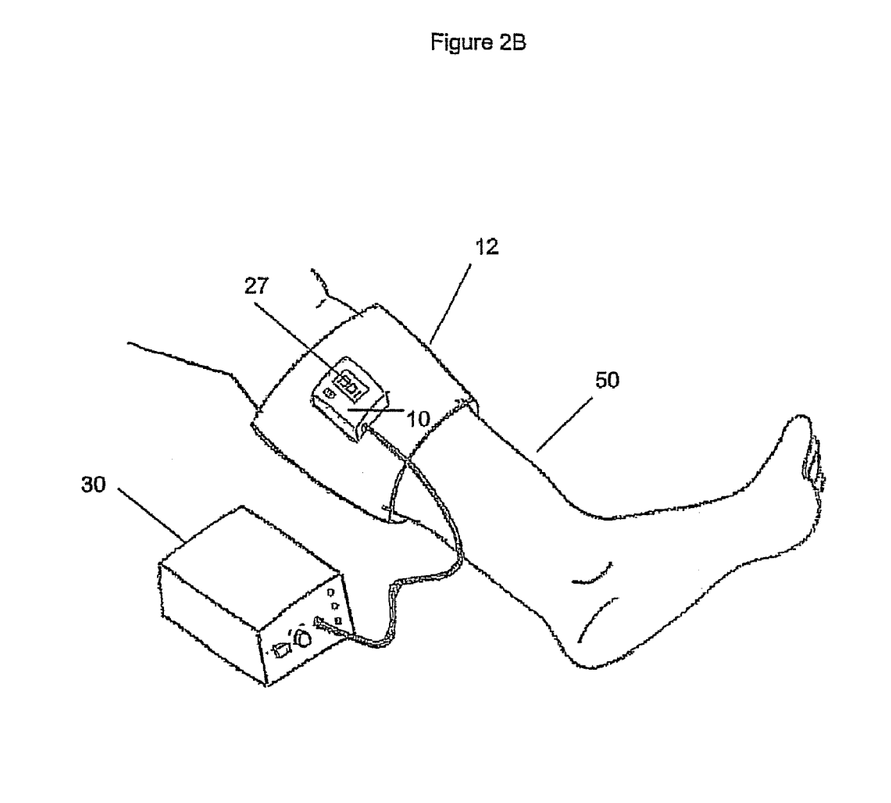
Figure 3:
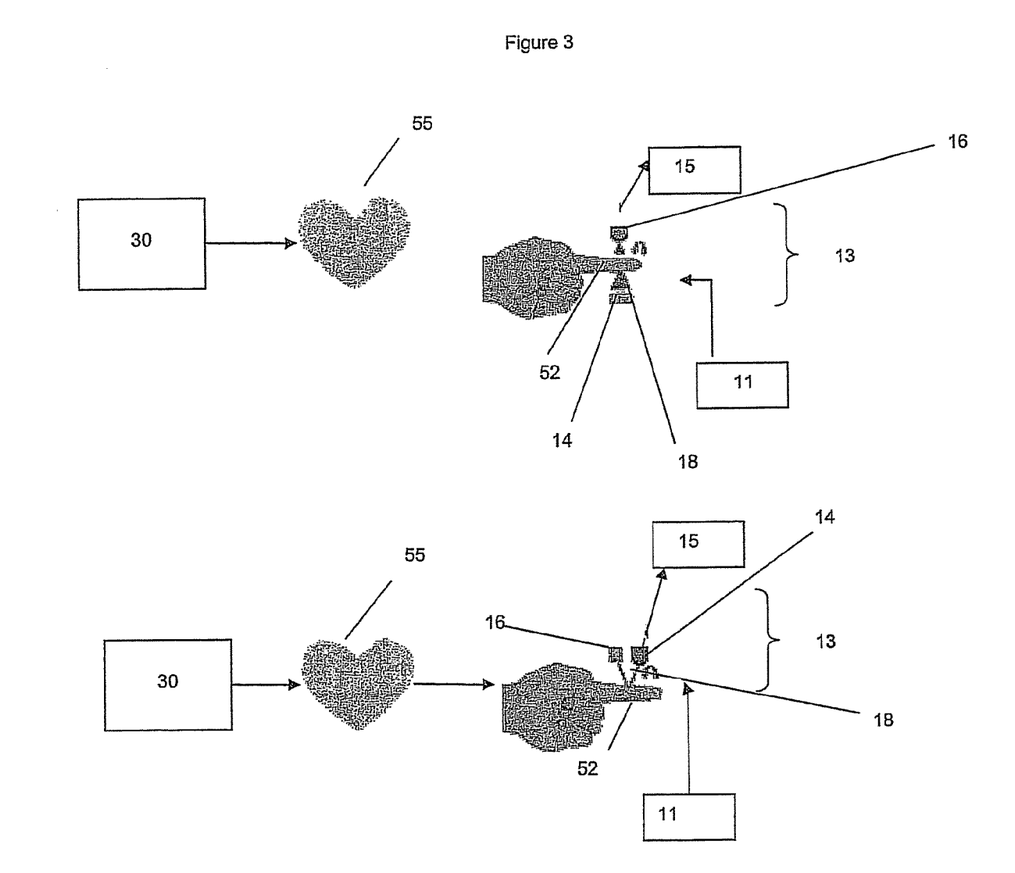
FIG. 3 shows schematics of an example of the claimed device.

FIGS. 2 and 3 show schematics of examples of embodiments of the device 10 of the present invention. In an example, device 10 is portable such that device 10 may be carried into challenging settings outside of the hospital such as in far forward military applications, in ambulances, and/or by emergency response personnel. In examples, device 10 may be attached to a hospital bed 70 (see FIG. 2A), a gurney (not shown), a wheelchair (not shown), or a part of the subject's 50 body (see FIG. 2B, described in greater detail below). As shown in the figures, and referring particularly to FIGS. 2-3, the claimed device 10 is comprised of a controller or a control 11, a transducer 13, and a processor 15. The controller 11 initiates collection of a plurality of data related to a physiological condition. In an example, the physiological condition is related to the subject's 50 cardiovascular system, or is indicative of dysfunction of the subject's 50 cardiovascular system, either directly or indirectly, such as is illustrated in the chart recordings and graph shown in FIG. 1. In this way, collected data related to the physiological condition provide an indirect index of cardiovascular dysfunction such that relative changes in the physiological condition may indicate cardiovascular dysfunction.

In examples, the controller 11 is a switch or a trigger that initiates data collection and that may be operated manually, automatically, or both. In another example, the controller 11 is a plurality of software rules that manage the data collection process. In another example, the controller 11 is a combination of the software rules and at least one of the switches.

Figure 7:
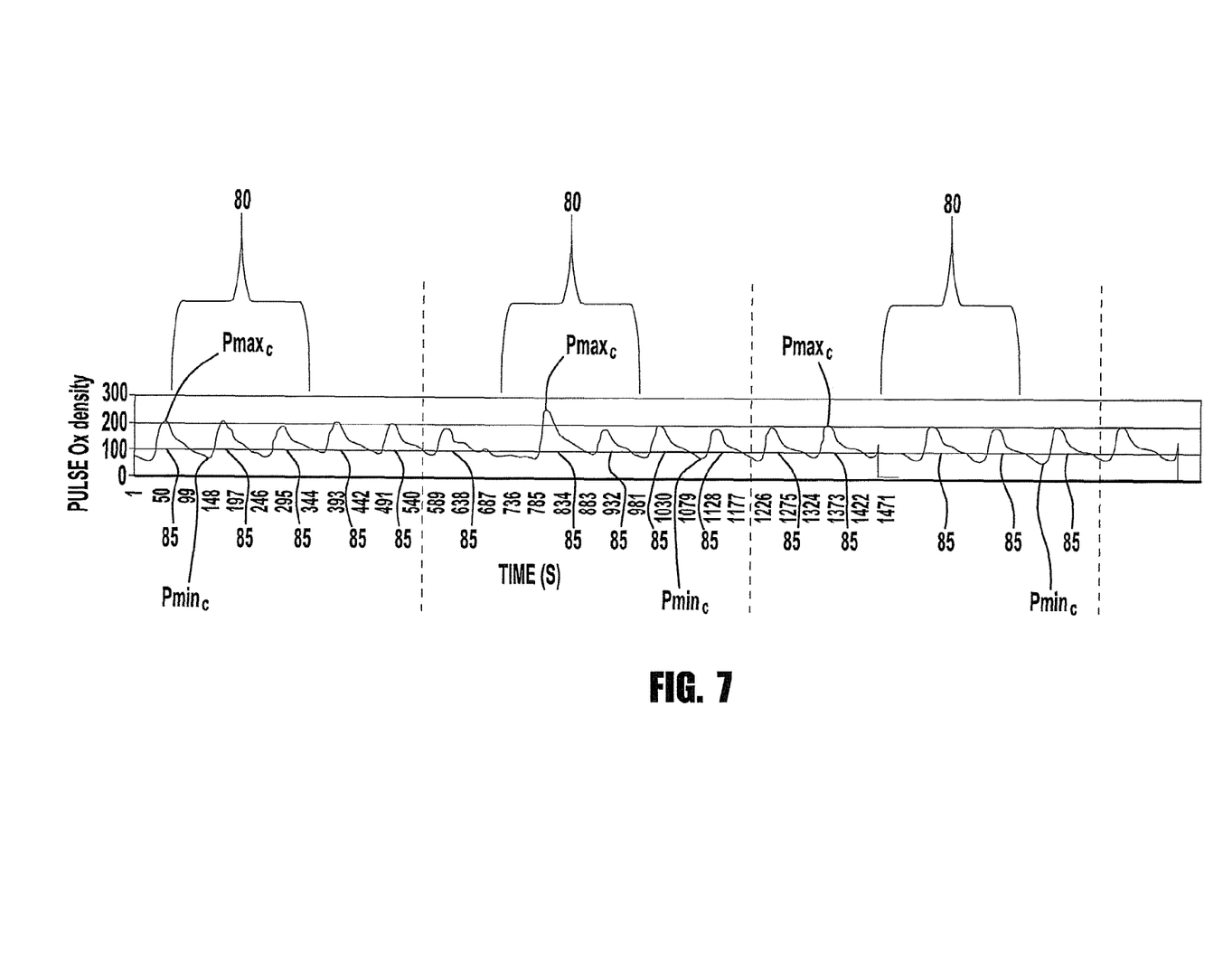
FIG. 7 shows a chart recording of pulse oximeter density collected during a perturbation.

The transducer 13 continuously collects data over a plurality of cycles 80 (see FIG. 7). In an example, there is also a plurality of subcycles 85 within each cycle. For example, cycles 80 may be respiratory cycles and within each respiratory cycle there may be a plurality of cardiac cycles. Transducer 13 transfers or transmits data to the processor 15. Transducer 13 may be any component that is capable of converting energy into a useable physiological signal. In examples, transducer 13 is comprised of analog-to-digital converter processing and algorithms to convert energy into a usable physiological signal, such as for example the measure of oxygenated hemoglobin as represented by a pulse pressure chart recording of pulse oximeter density (see FIGS. 1A and 1B). In examples, the transducer is a photoplethysmograph (see FIG. 3) that utilizes either absorbed (FIG. 3A) or reflected (FIG. 3B) light waves. Other examples of transducers 13 include impedance cardiographs, ultra wide-band radar, esophageal pulse Doppler, or thermodilution. This list is not intended to be limiting however, and transducer 13 may include any component that does not interfere with the intended purpose of the claimed invention.

The processor 15 receives the data signal from the transducer 13 and reduces or processes the data signal into at least one output 20 by at least calculating a variation of the data signal across the cycles over which data were collected. In an example, the processor 15 applies a filter to capture the maximum and minimum data signal in each subcycle 85 to assess and treat cardiovascularly unstable patients 85 and the mean of the maximum data signals and minimum data signals across all cycles 80, and uses a formula to calculate the deviation of the signal across all cycles 80. The use of this formula imparts on the device 10 a level of sensitivity to detect change in the physiologic condition previously unavailable to non-invasive devices.

In an example, the formula is embodied in software rules. The formula is as follows:

$$\text{percent deviation}_{data\ signal} = (P\text{mean}_{max} - P\text{mean}_{min}) / [(P\text{mean}_{max} + P\text{mean}_{min})/2] \times 100.$$

In this formula, percent deviation$_{data\ signal}$ is a variation in a data signal received from the transducer 13. Pmean$_{max}$ is a maximum mean value of the data signal across the plurality of cycles 80, and Pmean$_{min}$ is a minimum mean value of the data signal across the cycles 80. A mean value of the data signal is calculated for each subcycle (c) 85 as follows:

$$P\text{mean}_c = P\text{max}_c + P\text{min}_c/2.$$

In this formula, and referring to the example chart recording shown in FIG. 7, Pmax$_c$ is the maximum data signal in a given subcycle (c) and Pmin$_c$ is the minimum data signal in a given subcycle (c). Pmean$_{max}$ and Pmean$_{min}$ are the highest and lowest mean value of the data signal, respectively, out of all of the Pmean$_c$ calculated (i.e., one Pmean$_c$ for each of the subcycles (c)).

While an embodiment of the present invention contemplates that the output 20 is a percent deviation in the data signal, output 20 may also be the plurality of data collected, the data signal itself, an information set, an interface, or a combination thereof. In other examples, output 20 is an interpretation of data signal and may optionally suggest action or treatment protocols. Any output may be graphical, numerical, or textual.

Output 20 may be displayed remotely, on device itself, and/or may be integrated with an interface such as the one shown in FIG. 4 and described in detail below. In examples, the output 20 is displayed on a handheld device, a monitor screen 25 (see FIG. 4), a display window 27 (see FIG. 2B), and/or any other display means known in the art that does not interfere with the intended use of the claimed invention. As shown in the example in FIG. 4, output is displayed on a monitor 25 and is integrated with an interface system that provides, for example, subject-specific information such as direct cardiovascular measurements, analytics, transducer signal quality, and patient status. In an example, output 20 is interpretations of gauges and measures that would enable a caregiver at any level of competency to interpret the analysis and to determine an appropriate action, such as treatment protocol. In an example, the interpretation indicates that the subject is deficient and the form of the deficiency related to norms. Other examples of information that may be displayed as part of the interface include biographical information about subject such as name, patient number, age, gender, medical history, and known allergies to pharmacological agents. In an example, the output 20 is an objective directive for at least one proposed treatment protocol for treating the subject.

In an example, the device 10 of the claimed invention further comprises an activator 30. The activator 30 perturbs the cardiovascular system of the subject 50 in order to assess the cardiovascular system's response (i.e., the percent deviation$_{data\ signal}$) to the perturbation and to use that response or percent deviation$_{data\ signal}$ to identify cardiovascular insufficiency. In this way, in an example, the claimed device collects the data signal before, at the beginning of, and/or after the perturbation. In examples, the activator 30 is administration of an agent, a physical maneuver, and/or mechanical ventilation of the subject. Where the activator 30 is an agent, examples include but are not limited to administration of a bolus volume infusion or a pharmacologic agent such as a vasoconstrictor, a vasodilator, or a vasoactive agent, including for examples norepinephrine, epinephrine, and atropine. Where the activator 30 is administering a physical maneuver, examples include but are not limited to raising a subject's leg about 30% from resting position, compression of a part of the subject's body, such as a calf (see compression device shown in FIG. 2B and described below) or the abdomen, the Valsalva maneuver, or a change in physical position of the subject, such as going from a sitting to a standing position. The activator 30 may be activated by an automatic or manual switch or trigger, or by a motion sensor to recognize physical maneuvers.

In the example shown in FIG. 2A, the device 10 is portable and may be attached to a hospital bed 70. The device 10 (i.e., the controller 11, the transducer 13, and the processor 15) is embodied within a small box, and in an example, the activator 30 and the output display, shown here as a monitor 25, are embodied within the same box. In other examples, the activator 30 and/or output display are remote.

In the example shown in FIG. 2B, the device 10 is an inflatable cuff 12 that may be worn around the subject's calf. In an example, an automated or manual controller 11 initiates collection of data by the transducer 13 continuously over a plurality of cycles 80. The transducer transfers 13 the data to the processor 15 as a data signal and the processor 15 reduces the data signal into at least one output, as described above. In an example, an activator 30 inflates the cuff 12 (i.e., a cardiovascular perturbation) such that the inflation causes an intravascular volume load equivalent to a change of approximately 300 mL of volume in the subject's cardiovascular system. The percent deviation$_{data\ signal}$ is calculated by the processor 15 in response to the perturbation as described above. As shown in the example in FIG. 2B, the activator 30 is remotely connected to the device 10 by wired or wireless communication. In another example, the activator is not remote (not shown). In this example, the output display is a display window 27.

Another schematic of an example of the claimed device 10 is shown in FIG. 3. In this example, the transducer 13 is a photoplethysmographic device comprised of a photosource 14 and a photodetector 16. A controller 11 initiates collection of pulse oximeter density, which is a measure of the amount of oxygenated hemoglobin present in the subject's blood. The activator 30 perturbs the cardiovascular system 55. The photosource 14 emits light waves 18 of a known wavelength that pass through the vascular bed of a part of the subject's body such as a fingertip 52, as shown in FIG. 3A. As shown in FIG. 3B, in another example light waves are reflected off a surface of the fingertip 52. The photodetector 16 measures the amount of oxygenated hemoglobin in the subject's blood over the plurality of cycles 80.

Figure 5A:
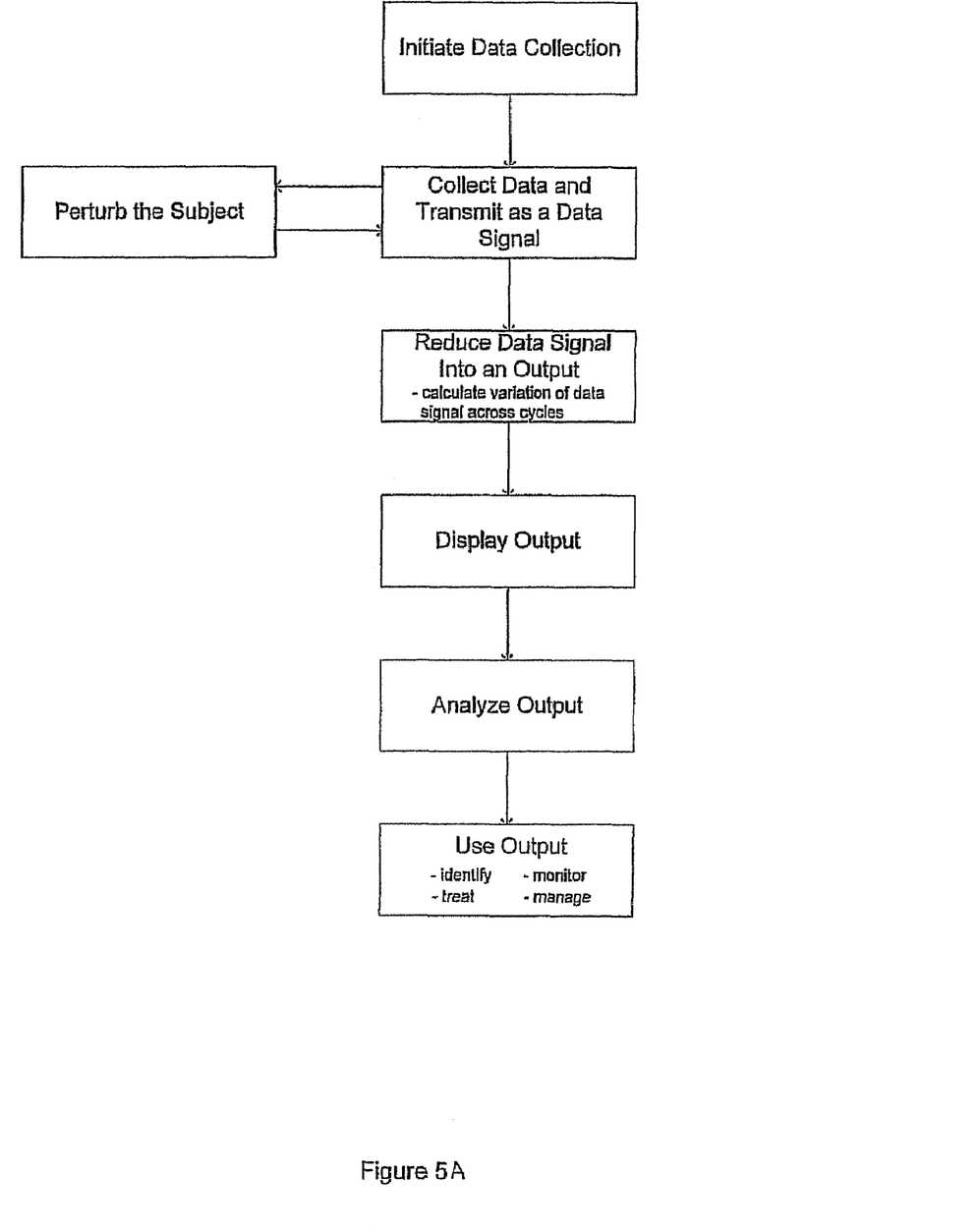
FIGS. 5A and 5B show schematics outlining the steps of an example of a method using the device of the claimed invention.

In an example of an embodiment, the claimed invention is a method of using the device 10 described above to identify cardiovascular insufficiency of a subject 50. In other examples, the claimed device is used to monitor a subject 50 (remotely or non-remotely), identify when the subject is hypovolemic or dehydrated (i.e., has decreased circulatory blood volume), manage a subject 50, and/or to institute a treatment protocol. Examples of use are provided in detail below. A schematic outlining the steps of an example of the claimed invention is depicted in FIG. 5.

In an example, the claimed method comprises the first step of initiating the collection of a plurality of data. In an example, data relate to a physiological condition of the subject 50, as described above. Data collection may be initiated by the controller 11 described above. In the example shown in FIG. 5, data collection need only be initiated one time because collection occurs continuously over the plurality of cycles 80. In other examples, such as where initiation is manually driven, the step of initiating data collection will be required every time data collection is desired or required.

The claimed method also comprises the step of collecting data. Collection is made by a transducer 13 such as the one described above. Examples of cycles 80 and subcycles 85 are identified in the chart recording shown in FIG. 7. As shown, data are collected across a plurality of cycles 80, such as respiratory cycles, and across sub-cycles 85 within each cycle, such as cardiac cycles.

The claimed method also comprises the step of reducing the received data signal into output. In an example, data are collected and subsequently reduced before, at the initiation of, and/or after a perturbation (described below). The processor 15 calculates at least a variation to generate an output and may make additional calculations. In the claimed method, the processor uses the formula described above to process the data signal.

In a next step, the subject's cardiovascular system is perturbed, for example by an activator 30. In another example, a healthcare provider 90 or a researcher perturbs the subject's cardiovascular system by performing a physical maneuver on the patient or by instructing the subject to perform such a maneuver. In other examples, an agent such as a bolus volume load or a pharmacological agent is administered to the subject. Perturbations include but are not limited to those described above.

Figure 4:
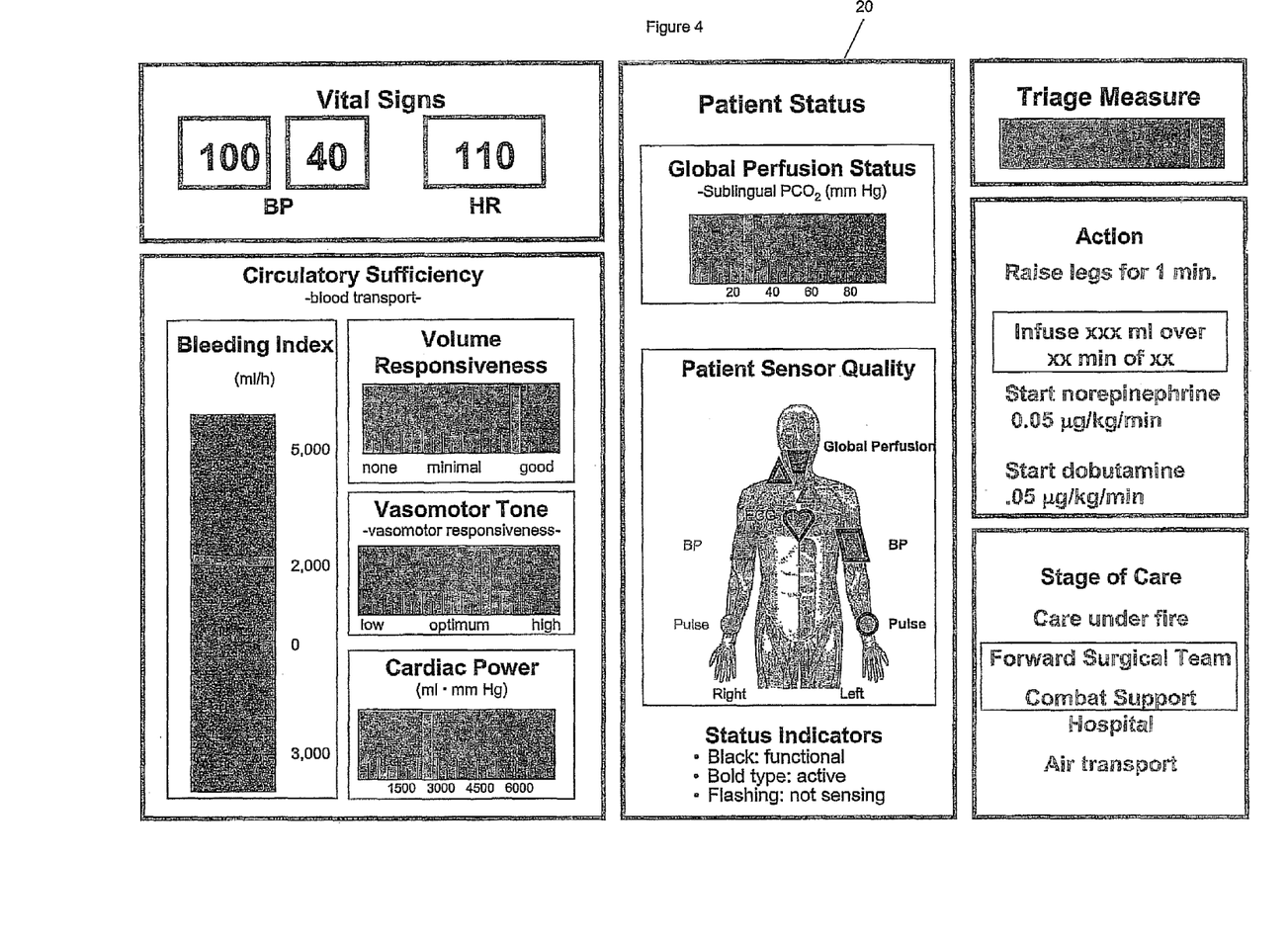
FIG. 4 shows an example of an embodiment of an output from the claimed device.

Referring still to FIG. 4, the next step of an example of a method of using the claimed invention is analyzing the output. In an example, the step of analyzing the data may be carried out by the processor 15 or by the healthcare provider 90 or both. For example, a physician treating the subject may analyze the data signal, and/or the calculated percent deviation. In another example, the processor 15 analyzes the signal and sends graphics that portray analytics or trends, gauges or meters, alarms, or any combination thereof, to a display monitor. In another example, the processor 15 recommends a treatment protocol that suggests how subject 50 should be treated. This recommendation may be displayed on an output interface such as the one shown in FIG. 4. In examples, analysis comprises the steps of comparing data or calculated deviations and deciding how to use the output.

Another step in an example of the claimed method is using the output to treat, monitor, or manage a subject 50, or to identify a physiological insufficiency in the subject, such as a cardiovascular insufficiency.

Figure 5B:
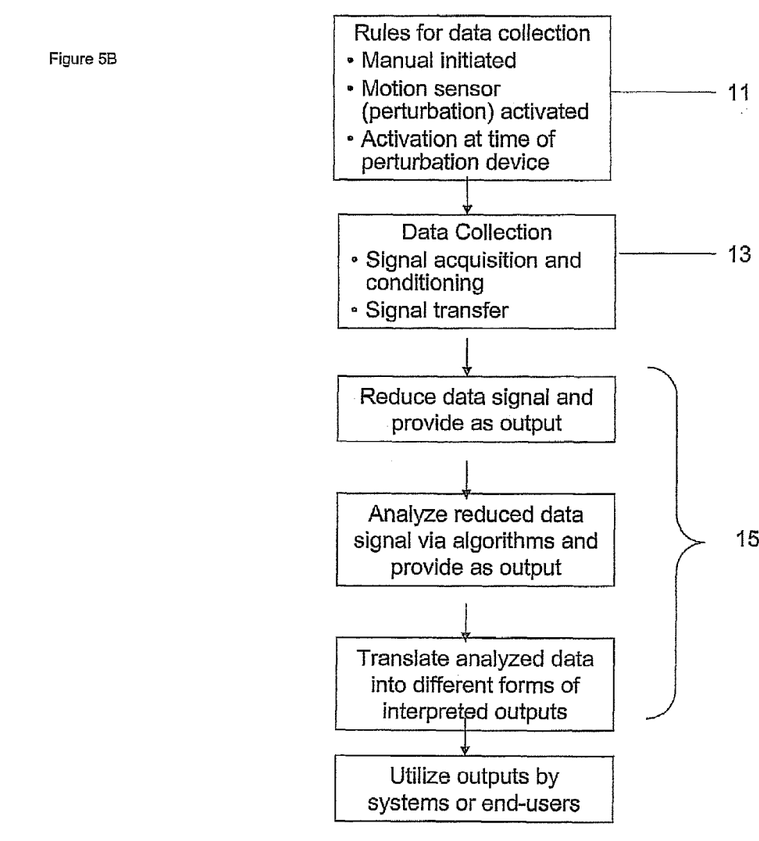

Another example of the method of using device 10 is shown in FIG. 5B. As shown, in a first step controller 11 operates using a set of rules. Controller 11 is manually initiated and a motion sensor is activated. Transducer 13 collects data and acquires and conditions the signal to be transferred to processor 15. Processor 15 reduces the signal such as by using the formula described above and provides an output. In a next step, the analyzed signal is translated into any type of output, including the examples described above. The output is then used by a system or user, such as a physician 90, researcher, or leader.

Although the schematics in FIG. 5 show examples of the claimed method, the steps of the claimed method may be carried out in any order and may optionally be repeated at least one time.

In alternate embodiments, the inventive method can be embodied in a system 100 such as the one shown in FIG. 6, described below. In an embodiment, the system 100 is a computer system, although the system may be implemented in any combination of hardware and software, as long as the combination does not interfere with the scope and intended use of the claimed invention. In an example, the system comprises a subject 50, a device 10 such as the one described above, and a healthcare provider 90, researcher, or leader, such as a lead fire-fighter or a military superior. The device has a storage medium that stores instructions (not shown), a controller 11 that initiates data collection from the subject, a transducer 13 that collects and transfers data, and a processor 15 unit that reduces the data and uses the instructions to carry out at least one of a plurality of steps. In an example, the instructions carry out at least one of the steps of initiating the controller 11 to collect data, instructing the transducer 13 to collect data and transfer a data signal, perturbing the subject 50, processing the data into at least one output 20, analyzing the output 20, displaying the output 20, or deciding how to use the output 20. In an example, the healthcare provider 90 or researcher review the output and/or use the output to institute a treatment protocol, such as where the subject is cardiovascularly insufficient or hypovolemic. In other examples, the healthcare provider monitors or manages the subject 50, for example, from a remote location, as described above.

The processor 15 may contain a single microprocessor, or may contain a plurality of microprocessors for configuring the computer as a multi-processor system. The storage medium, or main memory, stores in part instructions and data for execution by the processor unit. If the method is implemented in software, the main memory stores the executable code when in operation. The main memory may be in the form of dynamic random access memory or any storage medium known in the art.

Figure 6:
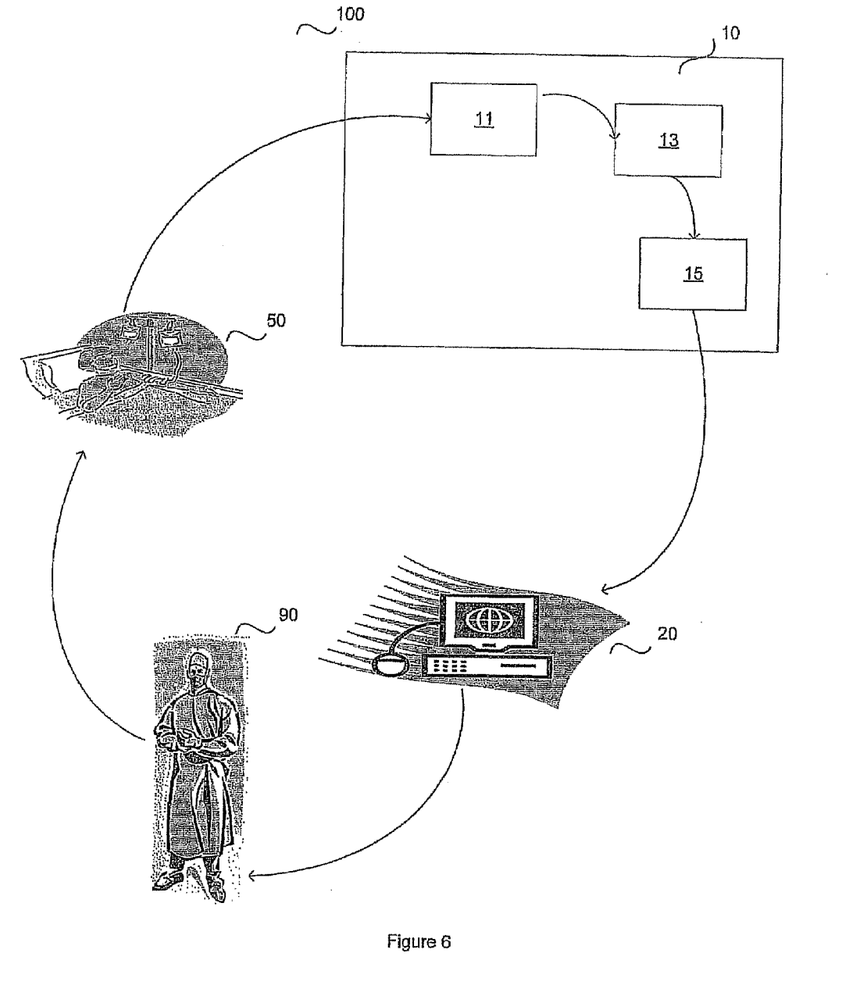
FIG. 6 shows a schematic of an example of a claimed system.

In the example system shown in FIG. 6, a data signal is transferred to the processor 15 by the transducer 13, such as for example a photoplethysmograph, that supplies data regarding a physiological condition of the subject. The processor 15 reduces the data and uses instructions (not shown) to carry out at least one of the steps of the claimed invention, shown in FIG. 4 and described in detail above. These steps generate an output. Output may be any output that a researcher 90 or a healthcare provider uses to either identify, treat, manage, or monitor a subject. Output includes at least the examples described above but may be in any form that could be used in a clinical or research setting.

The claimed system 100 may further include a mass storage device, peripheral devices, portable storage medium drives, input control device, a graphics subsystem, and an output display (not shown). The system 100 may be connected through one or more data communications means. For example, the processor and the main memory may be connected via a local microprocessor bus, and the mass storage device, peripheral devices, portable storage medium drives, graphics subsystem may be connected via one or more input/output (I/O) busses. The mass storage device, which may be implemented with a magnetic disk drive or an optical disk drive, is a non-volatile storage device for storing data and instructions for use by the processor. In the software embodiment, the mass storage device stores the information software for loading to the main memory.

The transducer 13 provides a portion of the user interface for a user of the computer system. The components contained in the computer system are those typically found in general purpose computer systems, and in fact, these components are intended to represent a broad category of such computer components that are well known in the art.

EXAMPLES

The following examples are intended to illustrate the claimed invention and should not be construed as limiting the invention in any way.

Example 1

Unattended Monitoring in an Active Individual

A military war-fighter is in a combat situation in a hot, dry climate such as a desert. The war-fighter is clothed in a military combat uniform and is carrying on his back weapons and packs full of supplies and ammunition. He has not had fluids for more than three hours and is therefore susceptible to dehydration. The claimed device continuously and periodically monitors the soldier. The war-fighter is equipped with a motion sensor somewhere on his person that indicates when a physical motion has been performed initiating data collection. Either software rules applied to the motion sensor signal, software rules applied to the transducer, or a combination thereof provide a data quality indicator software bit to the device rules for when an ample physical motion provides an adequate perturbation to the cardiovascular system. Based on this quality indicator, the claimed continuously-monitoring device utilizes the current sampled signal of oxygenated hemoglobin continuously over five respiratory cycles in order to monitor the soldier's vascular volume. When the output from the claimed device indicates that the soldier is near or in a dehydrated or hypovolemic state, a alarm is initiated (e.g. a vibration, a sound, a light) to either alert the warfighter that he needs to rehydrate himself or is communicated to others.

The device may be similarly used in other situations in which individuals are subjected to extreme environments, such as fire-fighters and astronauts.

Example 2

Unattended or Attended Monitoring of an Immobile Patient

A patient afflicted with a chronic cardiovascular condition requires home healthcare where a telehomecare service is provided for remote caregiver monitoring. In another instance an individual has an acute cardiovascular condition and requires emergency medical technician assistance. The claimed device, such as the one shown in FIG. 3, is equipped with a compressible cuff (i.e. sequential compression device or SCD), commonly employed in hospitals to limit venous stasis to mimic the perturbation from passive leg raising) that the patient wears around his calf when in bed, on a stretcher or gurney such as the ones shown in FIG. 2B, above. The cuff is automatically inflated periodically to create a perturbation to the cardiovascular system. The device monitors oxygenated hemoglobin levels continuously over five respiratory cycles beginning at the point in time of the perturbation in order to monitor the change of pressure or volume of the vasculature and assessed for cardiovascular insufficiency and potentially contributions to cardiovascular insufficiency using the entire hemodynamic algorithm and additional devices (e.g. blood pressure). An output is continuously periodically updated with a current output every time the medical device performs a perturbation followed by an assessment.

One form of the output could be a graphical display of a "patient dashboard" that provides interpreted results in easy-to-understand graphic metaphors such as a visual of a gauge or meter. This will allow caregivers of lesser competencies to apply complex hemodynamic concepts that indicate cardiovascular dysfunction such that more metabolically precise treatment protocols may be applied in a more responsive manner. Another output of the device may be an alarm of some type when the device has determined an extreme measure of cardiovascular dysfunction.

The output may be displayed at the bedside in the instance that the immobile patient is being attended to by a caregiver such as in an emergency transport. In addition or alternatively, the continually refreshed output may be transmitted via a wireless data communication, telecommunication, or satellite link to a remote location for continuous monitoring.

Example 3

Attended Immobile Patient Management

A hemodynamically unstable immobile critical care patient is being continuously monitored in a hospital acute care setting. The patient is spontaneously breathing making a mechanical ventilator unnecessary. A protocol is being administered to correct the patient's hemodynamic instability via a pharmacologic agent based protocol. The compressible cuff is worn around the patient's calf as in Example 2. In addition to a transducer to obtain a measure of the change in arterial pressure, cardiac output, or intravascular flow, other transducers are also captured such as measures of mean arterial pressure (i.e. an automated blood pressure cuff) to enable both output of all traditional vitals and analyses of the contributions of hemodynamic dysfunction such as disclosed in U.S. Pat. No. 6,776,764 to Pinsky. An output may be in the form of a patient dashboard at the bedside, communicated via a wireless communications method to caregiver's hand held device or to a clinical information system, or any combination. In this example the device is used for ongoing assessment of an instituted protocol to enable protocol optimization and responsive patient management.

While certain embodiments and applications have been described above, the skilled artisan will appreciate that there may be other applications to which the invention is well suited.

What is claimed is:
1. A non-invasive device that identifies volume insufficiency in a patient, comprising:
   a. a transducer that records a pulse density signal from said patient during at least one respiratory cycle prior to administration of a cardiovascular volume load and during at least one respiratory cycle following administra- tion of said cardiovascular volume load, wherein each respiratory cycle includes a plurality of cardiovascular subcycles;

b. a controller that controls said transducer to initiate said record of said pulse density signal, said controller comprising at least one of the following:
   i. a manual or an automated switch;
   ii. a plurality of software rules; or
   iii. a combination thereof;

c. an activator that activates said cardiovascular volume load; and d. a processor that is configured to filter said pulse density signal to capture a maximum and minimum data point in each cardiovascular subcycle and to calculate a percent deviation of said pulse density signal across all of said cycles, said percent deviation reflecting a volume status of said patient, said percent deviation being calculated according to the following formula:

percent deviation$_{data\ signal}$=($P$mean$_{max}$−$P$mean$_{min}$)/ [($P$mean$_{max}$+$P$mean$_{min}$)/2]×100, wherein percent deviation$_{data\ signal}$ is a variation in said pulse density signal recorded by said transducer prior to said cardiovascular volume load and following said cardiovascular volume load, wherein Pmean$_{max}$ is a maximum mean value of said pulse density signal recorded during all of said cycles, wherein Pmean$_{min}$ is a minimum mean value of said pulse density signal recorded during all of said cycles, wherein each said mean value of said pulse density signal is calculated for each said cardiovascular subcycle (c), as follows:

Pmean$_c$=Pmax$_c$+Pmin$_c$/2, wherein Pmax$_c$ is a maximum pulse density signal in a given subcycle (c) and Pmin$_c$ is a minimum pulse density signal in said given subcycle (c).

2. A device as in claim 1 wherein said device is portable and/or wearable.

3. A device as in claim 1 wherein said activator is at least one of the following:
   a. a volume of fluid;
   b. a pharmacologic agent;
   c. a physical maneuver;
   d. a mechanical ventilation;
   e. a manual or an automated switch;
   f. a motion sensor;
   g. a compression device; or
   h. a combination thereof.

4. A device as in claim 3 wherein said physical maneuver is raising a leg of said patient by about 30%, a compression of a part of said patient's body, or a change in a physical position of said patient.

5. A device as in claim 3 wherein said pharmacologic agent is at least one of:
   a. a vasodilator;
   b. a vasoconstrictor;
   c. a vasoactive agent; or
   d. a combination thereof.

6. A device as in claim 1 wherein said processor is further configured to generate an output that is selected from the group consisting of a data set, said pulse density signal, an interface, an interpretation, and a suggested treatment or protocol.

7. A device as in claim 6 wherein said output is graphical, numerical, or textual.

8. A device wherein said output is displayed on at least one of the following:
   a. a remote display;
   b. a handheld display;
   c. a display on said device;
   d. a display integrated with an interface; or
   e. a combination thereof.

9. A device as in claim 1 wherein said transducer is a photoplethysmographic device.

10. A device as in claim 1 wherein said device is an inflatable cuff.

11. A method of using a device to identify volume insufficiency in a patient comprising the steps of:
    a. initiating a recording of a pulse density signal by a transducer during at least one respiratory cycle prior to administration of a cardiovascular volume load and during at least one respiratory cycle following administration of said cardiovascular volume load;
    b. activating administration of said cardiovascular volume load;
    c. filtering said pulse density signal to capture a maximum and minimum data point in each cardiovascular subcycle and to calculate a percent deviation of said pulse density signal across all of said cycles, said percent deviation reflecting a volume status of said patient, said percent deviation being calculated according to the following formula:

percent deviation$_{data\ signal}$=($P$mean$_{max}$−$P$mean$_{min}$)/ [($P$mean$_{max}$+$P$mean$_{min}$)/2]×100, wherein percent deviation$_{data\ signal}$ is a variation in said pulse density signal recorded by said transducer prior to said cardiovascular volume load and following said cardiovascular volume load, wherein Pmean$_{max}$ is a maximum mean value of said pulse density signal recorded during all of said cycles, wherein Pmean$_{min}$ is a minimum mean value of said pulse density signal recorded during all of said cycles, wherein each said mean value of said pulse density signal is calculated for each said cardiovascular subcycle (c), as follows:

Pmean$_c$=Pmax$_c$+Pmin$_c$/2, wherein Pmax$_c$ is a maximum pulse density signal in a given subcycle (c) and Pmin$_c$ is a minimum pulse density signal in said given subcycle (c), d. converting said pulse density signal to an output; and
e. analyzing said output to identify a volume status of said patient.

12. A method as in claim 11 further comprising the step of using output to:
    a. monitor said patient either remotely or non-remotely;
    b. manage said patient;
    c. institute a treatment protocol for said patient; or
    d. a combination thereof.

* * * * *